(12) United States Patent
Cech et al.

(10) Patent No.: US 7,909,464 B2
(45) Date of Patent: Mar. 22, 2011

(54) DIAGNOSTIC OPHTHALMIC LENS USING EXTRA-LOW DISPERSION (ED) MATERIAL

(75) Inventors: Steven D. Cech, Aurora, OH (US); Stephen Jon Lawn, Olmsted Township, OH (US)

(73) Assignee: Volk Optical Inc., Mentor, OH (US)

( * ) Notice: Subject to any disclaimer, the term of this patent is extended or adjusted under 35 U.S.C. 154(b) by 0 days.

(21) Appl. No.: 11/698,360

(22) Filed: Jan. 26, 2007

(65) Prior Publication Data

US 2007/0171371 A1    Jul. 26, 2007

Related U.S. Application Data

(60) Provisional application No. 60/762,275, filed on Jan. 26, 2006.

(51) Int. Cl.
*A61B 3/00* (2006.01)

(52) U.S. Cl. ........................................ 351/219; 351/216

(58) Field of Classification Search ................... 351/219, 351/216
See application file for complete search history.

(56) References Cited

U.S. PATENT DOCUMENTS

| 4,627,694 A | 12/1986 | Volk |
| 4,738,521 A | 4/1988 | Volk |
| 5,523,810 A * | 6/1996 | Volk .............................. 351/219 |
| 5,838,501 A * | 11/1998 | Fukumoto .................... 359/718 |
| 5,859,685 A * | 1/1999 | Gupta et al. .................. 351/159 |

OTHER PUBLICATIONS

International Search Report.

* cited by examiner

*Primary Examiner* — Jordan M. Schwartz
*Assistant Examiner* — James C Jones
(74) *Attorney, Agent, or Firm* — Fay Sharpe LLP

(57) ABSTRACT

An improved diagnostic ophthalmic lens using extra-low dispersion material, defined by having an Abbe Number, $V_d > 80$, is provided. Such a single element diagnostic ophthalmic lens may be used for examination of the eye in conjunction with either an Indirect Opthalmoscope or a Slit Lamp Biomicroscope.

18 Claims, 3 Drawing Sheets

DIAGNOSTIC OPHTHALMIC LENS USING EXTRA-LOW DISPERSION (ED) MATERIAL

This application is based on and claims priority to U.S. Provisional Application No. 60/762,275, filed on Jan. 26, 2006, which is hereby incorporated herein by reference in its entirety.

FIELD

The presently described embodiments are directed to diagnostic ophthalmic lenses, particularly lenses used for examination of the eye via indirect ophthalmoscope or a slit lamp biomicroscope. For the purposes of describing at least one form of the presently described embodiments, the diagnostic lens is, for example, a singlet, made from Extra-low Dispersion (ED) material, defined by Abbe Number, $V_d > 80$, and mounted in a mechanical housing to form a lens device or assembly.

BACKGROUND

Dispersion of a material is its variation of refractive index (n) with respect to wavelength ($\lambda$). For visible light, most transparent materials have the following relationship between the changes in its index of refraction (n) verses wavelength ($\lambda$):

$$\frac{dn}{d\lambda} < 0.$$

It follows from this relationship that as the wavelength ($\lambda$) increases, the material's index of refraction (n) decreases. Thus, at a material interface, such as air-to-glass, the angle at which light is refracted will vary with wavelength, causing an angular dispersion of colors. For imaging over a wide spectrum, such as the visible, this introduces chromatic dispersion. This shows up in imaging as chromatic aberration, which degrades performance and image quality of the lens. Thus, lowering the dispersion in an optical design can greatly improve the overall image quality that a lens provides.

One way to define a material's dispersion properties in the visible region is known as the Abbe Number (or V-Number). The Abbe Number of a transparent material can be represented in a number of ways, the most common in many applications defines the relationship of the indices of refraction (n) in a given material as:

$$V_d = \frac{n_d - 1}{n_F - n_C}$$

where d is the yellow Fraunhofer helium-d line (at a wavelength of 587.6 nm), while F and C are the Fraunhofer spectral lines (486.1 nm and 656.3 nm respectively). This relationship shows that materials with a high Abbe Number ($V_d$) have low dispersion, making them attractive in optical designs that require chromatic dispersion correction.

Further, an Abbe Diagram or "glass map" can be constructed by plotting Abbe Numbers ($V_d$) of materials versus refractive index ($n_d$). Such diagrams or maps are typically provided by manufacturers in the field. This allows materials, and more commonly glasses, to be easily categorized based on their properties and composition. For example, flint glasses are defined as those having $V_d < 50$, with a very dense flint glass having $V_d$ around 20. Crown glasses are defined as those having $V_d > 50$, with very light crown glasses having $V_d$ values up to 65. In order to achieve even higher Abbe Numbers and, thus, lower dispersion in glass form, it was necessary to introduce fluoride compounds into glass melts to allow glass to approach the optical properties of fluorites. Fluorites, such as Calcium Fluoride ($CaF_2$), Lithium Fluoride (LiF), etc., typically have very high Abbe Numbers, but are crystalline in structure, which tends to make them very soft and susceptible to fractures and etching. So, while their optical properties are desirable, mechanically they are not desirable when lens surfaces are exposed to the outside environment. This resulted in glass manufacturers developing fluorite-like glass, creating a new category of glass called fluor-crowns or Extra-low Dispersion (ED) glass. They have the same favorable optical properties of fluorites in that they have low dispersion, but do not have a crystalline structure. So, they exhibit improved mechanical properties over fluorites and are less susceptible to fractures and harsh environments. These Extra-low Dispersion glasses have come to be defined as glasses with an Abbe Number $V_d > 80$, the same region that most fluorites fall under. The Japanese glass manufacturer Ohara Corp., as an example, currently produces three types of Extra-low Dispersion glass: S-FPL51 ($n_d = 1.497$, $V_d = 81.6$), S-FPL-52 ($n_d = 1.456$, $V_d = 90.3$), and S-FPL-53 ($n_d = 1.43875$, $V_d = 95.0$).

In the field of Ophthalmology, it is well known that to perform a standard examination of a patient's internal eye structure, particularly the retina or fundus, the examiner typically uses a diagnostic ophthalmic lens in conjunction with either an indirect ophthalmoscope or a slit lamp biomicroscope.

U.S. Pat. No. 4,627,694, "Indirect Ophthalmoscopy Lens for Use With Slit Lamp Biomicroscope" describes a diagnostic ophthalmic lens design comprising a singlet made of a homogeneous transparent optical material having two aspheric surfaces of revolution, for use in conjunction with a Slit Lamp Biomicroscope. This patent is incorporated herein by way of reference.

U.S. Pat. No. 4,738,521, "Lens for Indirect Ophthalmoscopy" also describes a diagnostic ophthalmic lens design comprising a singlet made of a homogeneous transparent optical material having two aspheric surfaces of revolution, for use in conjunction with an Indirect Ophthalmoscope (either monocular or binocular). This patent is incorporated herein by way of reference.

These patents describe a basic concept for diagnostic ophthalmic lens designs: single lens elements made of a transparent optical material, for use in conjunction with indirect ophthalmoscopes and slit lamp biomicroscopes, in order to obtain an image of a retina or fundus for the purpose of performing an examination on a patient's eye. The diagnostic ophthalmic lenses cited must be placed (hand held or otherwise temporarily mounted) a defined and suitable working distance from the cornea of the patient's eye in order to perform two primary functions. First, it operates as a condensing lens converging light from a source found on either the indirect ophthalmoscope or the slit lamp biomicroscope, into the patient's eye, through the pupil, thereby illuminating the patient's retina. Secondly, the diagnostic ophthalmic lens forms an indirect image, located in a plane external to the eye structure itself, of the patient's retinal surface. This indirect image of the curved retinal surface forms a generally flat image plane, typically free of any significant image aberrations, wherein it becomes available for convenient observation by the examiner using either an indirect ophthalmoscope or a slit lamp biomicroscope.

The performance of these lenses, however, could be improved. In this regard, the presently described embodiments relate to an improved diagnostic ophthalmic lens and/or lens assembly or device.

SUMMARY

In one aspect of the presently described embodiments, an improved diagnostic ophthalmic lens design is provided that is, in one form, comprised of a single lens element that is fabricated from a material having an Abbe Number ($V_d$) greater than 80, including but not limited to fluor-crown glass, Extra-low Dispersion (ED) glass, fluorites, or polymers, that can be used in conjunction with an Indirect Ophthalmoscope to facilitate examination of a patient's eye. The optical power of the diagnostic ophthalmic lens for use with the Indirect Ophthalmoscope may be between about 10 and about 55 diopters.

In another aspect of the presently described embodiments, an improved diagnostic ophthalmic lens design is provided that is, in one form, comprised of a single lens element that is fabricated from a material having an Abbe Number ($V_d$) greater than 80, including but not limited to fluor-crown glass, Extra-low Dispersion (ED) glass, fluorites, or polymers, that can be used in conjunction with a Slit Lamp Biomicroscope to facilitate examination of a patient's eye. The optical power of the diagnostic ophthalmic lens for use with the Slit Lamp Biomicroscope may be between about 60 and about 130 diopters.

In another aspect of the presently described embodiments, a diagnostic ophthalmic lens assembly comprises a lens element formed from a material having an Abbe Number greater than 80 ($V_d$>80) and a housing in which said lens element is positioned.

In another aspect of the presently described embodiments, surfaces of the lens element are aspheric.

In another aspect of the presently described embodiments, surfaces of the lens element are spherical.

In another aspect of the presently described embodiments, one surface of the lens element is aspheric and another surface of the lens element is spherical.

In another aspect of the presently described embodiments, said lens assembly is used in conjunction with an Indirect Ophthalmoscope.

In another aspect of the presently described embodiments, the optical power of said lens element is about 10 to about 55 diopters.

In another aspect of the presently described embodiments, said lens assembly is used in conjunction with a Slit Lamp Biomicroscope.

In another aspect of the presently described embodiments, the optical power of said lens element is about 60 to about 130 diopters.

In another aspect of the presently described embodiments, the material is a fluor-crown glass.

In another aspect of the presently described embodiments, the material is extra-low dispersion glass.

In another aspect of the presently described embodiments, the material is a fluorite.

In another aspect of the presently described embodiments, the material is a polymer.

In another aspect of the presently described embodiments, the lens element is a single lens element.

In another aspect of the presently described embodiments, a method for forming a diagnostic ophthalmic lens assembly comprises forming a lens element for diagnostic ophthalmic use from an extra-low dispersion material and positioning the lens element within a housing.

In another aspect of the presently described embodiments, the method further comprises using the lens assembly in conjunction with an Indirect Ophthalmoscope.

In another aspect of the presently described embodiments, the method further comprises using the lens assembly in conjunction with a Slit Lamp Biomicroscope.

In another aspect of the presently described embodiments, the extra-low dispersion material has an Abbe number greater than 80.

In another aspect of the presently described embodiments, a diagnostic ophthalmic lens system comprises a lens element formed from an Extra-low dispersion material, and, a housing in which the lens element is positioned.

In another aspect of the presently described embodiments, the system further comprises an Indirect Ophthalmoscope.

In another aspect of the presently described embodiments, the system further comprises a Slit Lamp Biomicroscope.

Figure 1:
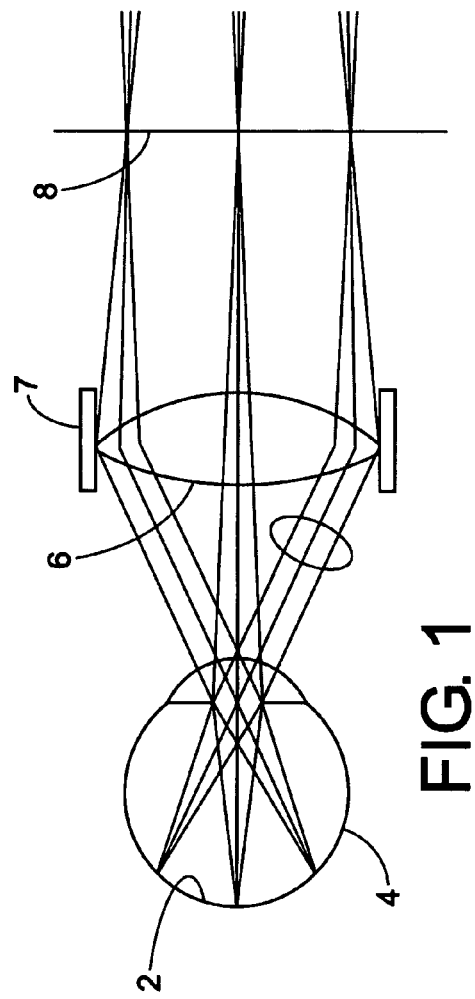
FIG. 1 illustrates the retinal image formation by a diagnostic ophthalmic lens of the presently described embodiments.

The embodiments set forth in the drawings are illustrative in nature and are not intended to be limiting of that which is defined by the claims. Moreover, individual features of the drawing and the embodiments will be more fully apparent and understood in view of the detailed description.

DETAILED DESCRIPTION

The presently described embodiments are directed to diagnostic ophthalmic lenses for use in the ophthalmic examination arena. The diagnostic ophthalmic lenses of the presently described embodiments may be used to form an inverted real aerial image of the retina or fundus and, when used in conjunction with an either an Indirect Ophthalmoscope or Slit Lamp Biomicroscope, allows the examiner to view the interior of the patient's eye.

The diagnostic ophthalmic lens of the presently described embodiments include, in one form, a single lens element fabricated from an Extra-low Dispersion (ED) material, defined by Abbe Number, $V_d$>80, including but not limited to fluor-crown glass, Extra-low Dispersion (ED) glass, fluorites, or polymers that meet the criteria. The lens element is typically positioned in a housing (an example of which is described in detail in FIGS. 4 and 5) to form a lens device or assembly.

In particular, the applicant has discovered that diagnostic ophthalmic lenses comprising a single lens element made from a material having an Abbe Number, $V_d$ greater than 80, will significantly reduce chromatic dispersion and, therefore, reduce the chromatic aberration in resulting images, as compared to lens elements made from materials having a lower Abbe Number and, thus, higher dispersion properties.

Figure 2:
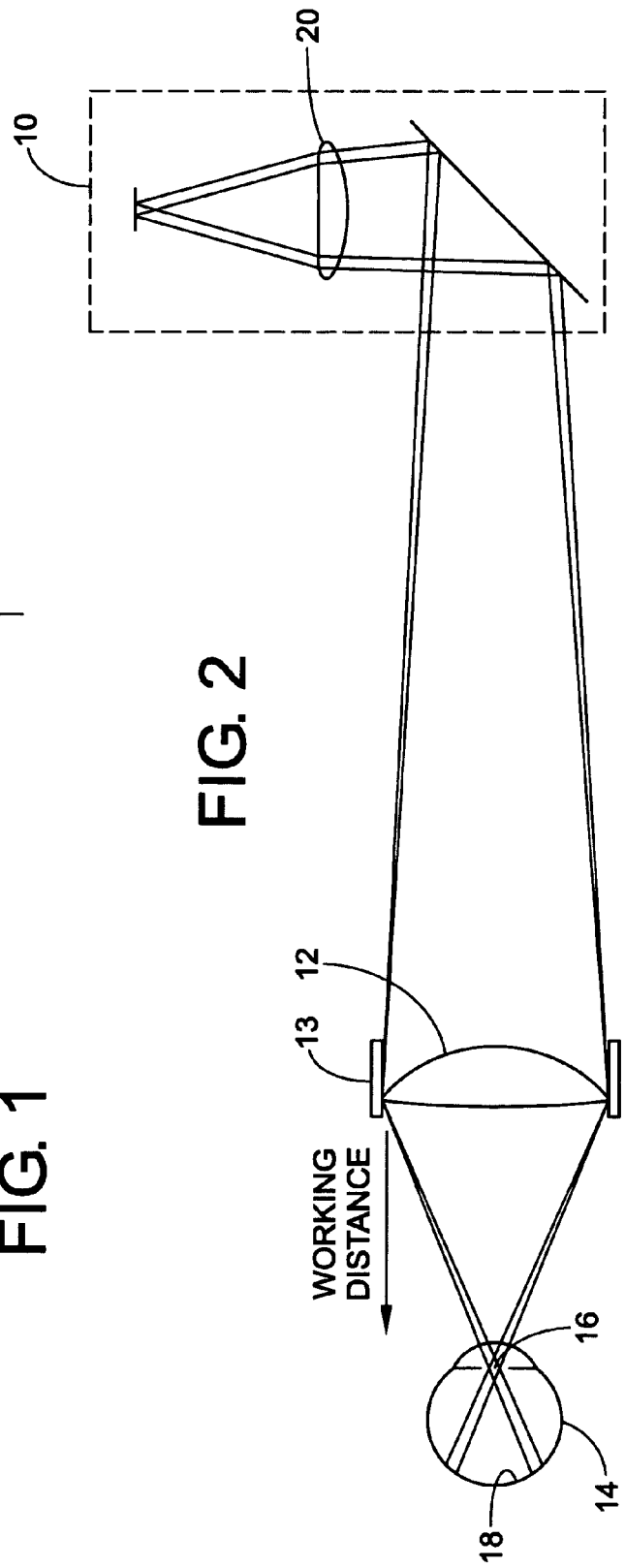
FIG. 2 illustrates the use of a diagnostic ophthalmic lens of the presently described embodiments with either an indirect ophthalmoscope or a slit lamp biomicroscope.

FIGS. 1 and 2 illustrate exemplary systems or environments into which the presently described embodiments may be implemented. As noted, it should be appreciated that the lens, or lens device or assembly, is typically manually manipulated by an examiner in conjunction with the noted optical devices. However, in some cases, the lens (or lens assembly or device) may be provided with a suitable mounting structure.

FIG. 1 depicts a schematic representation of the formation of the image of the illuminated retina or fundus 2 of the eye 4 using a diagnostic ophthalmic lens 6 according to the presently described embodiments. Also shown is a housing 7 into which the lens (or lens element) is positioned to form an assembly (or device). The image 8 of the retina or fundus is shown to be essentially flat, and is formed in the focal plane of either the indirect ophthalmoscope or a slit lamp biomicroscope where it can be viewed by the examiner for patient examination.

FIG. 2 depicts the use of the presently described embodiments with an Indirect Ophthalmoscope or Slit Lamp Biomicroscope 10 to form an indirect image of a retina. In FIG. 2, a diagnostic ophthalmic lens 12 is located at a distance from an eye-under-exam 14. A housing 13 for the lens 12 is also shown. The Indirect Ophthalmoscope or Slit Lamp Biomicroscope 10 includes a lamp (not shown) having an associated illumination path. The lamp acts as a source of illumination, which highlights the surface of the retina in order to form the indirect, real retinal image. Light emitted from the lamp travels along the illumination path until it strikes the surface of the diagnostic ophthalmic lens. At this point, the diagnostic ophthalmic lens focuses the light through the pupil 16 of the eye 14 and onto the retinal surface 18. The lens 12 then receives reflected light rays from all points along the surface of the retina 18 and forms an inverted and magnified indirect image of the retinal surface in a region external to the eye. After forming the indirect image, the imaged light rays proceed towards an indirect ophthalmoscope 10 along an imaging path. At the indirect ophthalmoscope or slit lamp biomicroscope 10, the light rays that have followed along the imaging path are received by the objective lens 20 of the indirect ophthalmoscope or slit lamp biomicroscope, which acts, in turn, to make the retinal image viewable by the doctor.

Figure 3:
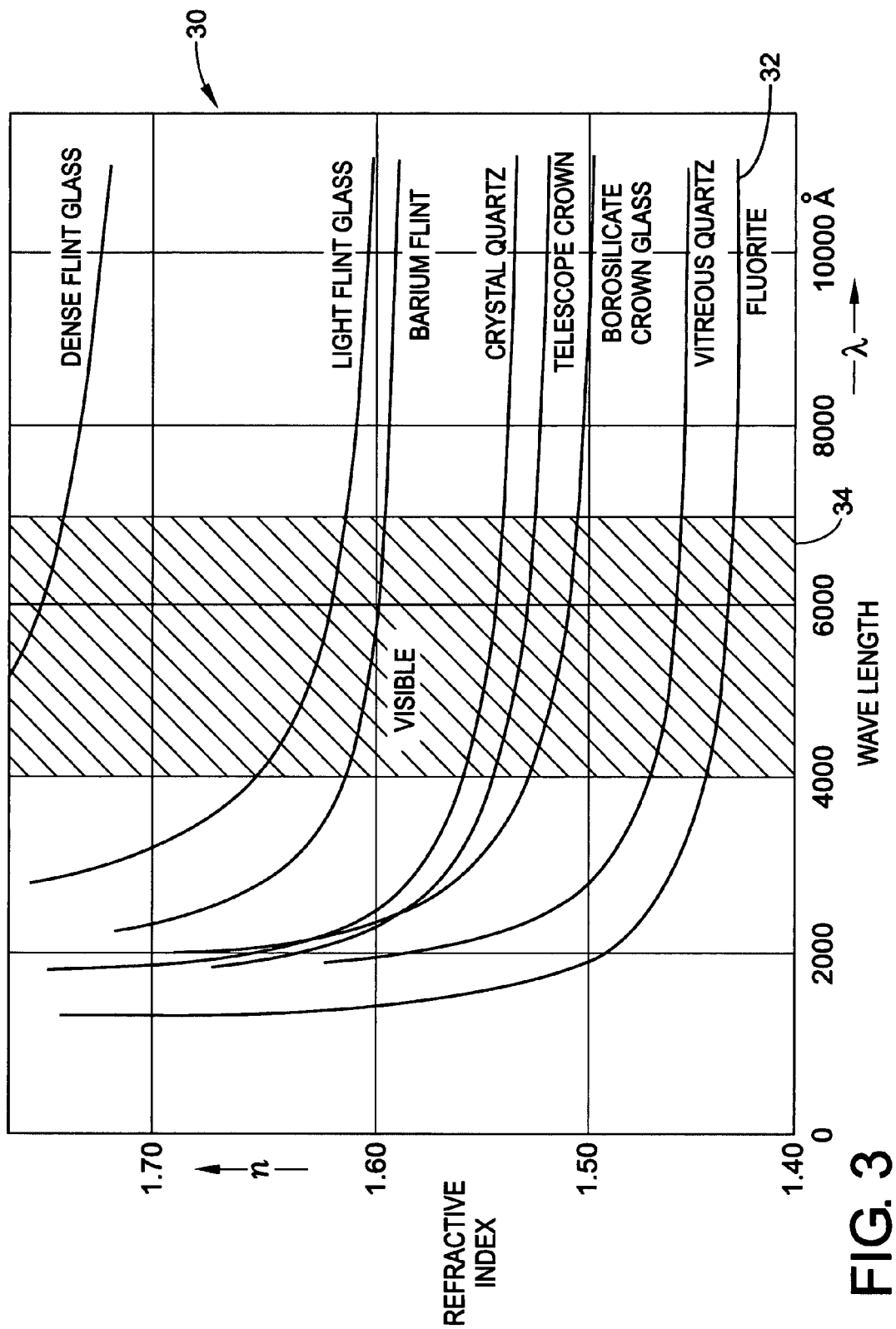
FIG. 3 shows a graphical representation of material dispersion via a plot of wavelength versus index of refraction.

FIG. 3 depicts a graphical representation 30 of material dispersion via a plot of wavelength versus index of refraction. Of particular note is the curve 32 marked "fluorite" that mimics the characteristics of materials with an Abbe Number greater than 80 used in the diagnostic ophthalmic lenses of the presently described embodiments. It also highlights the visible wavelength region 34 where the contemplated lens is designed for use. Note that the dispersion curve is flatter in this region compared to other material types commonly used for diagnostic ophthalmic lenses. The flatness of this curve indicates that materials of this category have a relatively low dispersion.

Historically, compositions used to fabricate diagnostic ophthalmic lenses were primarily high index of refraction and higher dispersion materials. The applicant has discovered that changing the material of the diagnostic ophthalmic lens to a low dispersion material can reduce the tendency of the lens to exhibit chromatic dispersion and in doing so improve its overall performance.

In particular, material compositions having an Abbe Number, $V_d$ greater than 80 allow the formation of a diagnostic ophthalmic lens resulting in less chromatic dispersion as compared to a lens fabricated out of a material with a lower Abbe Number and, thus, higher dispersion. Several material types are available that are suitable for fabricating lenses that have an inherent Abbe Number, $V_d$ greater than 80.

The following material types fall in the category of Extra-low Dispersion (ED), that represent a selection of materials that are currently commercially available. They are provided in the table below as an example:

| Glass Name | Manufacturer | $V_d$ | $n_d$ |
|---|---|---|---|
| $MgF_2O_2$ | Fluorite | 106.638 | |
| $MgF_2H_2$ | Fluorite | 104.966 | |
| S-FPL53 | Ohara | 94.994 | 1.439 |
| KF | Fluorite | 95.056 | |
| K-CaFK95 | Sumita | 94.848 | 1.434 |
| $CaF_2$ | Fluorite | 95.319 | |
| LiF | Fluorite | 98.757 | |
| S-FPL52 | Ohara | 90.342 | 1.456 |
| FCD10 | Hoya | 90.270 | 1.457 |
| K-PFK85 | Sumita | 85.174 | 1.486 |
| N-FK51 | Schott | 84.468 | 1.487 |
| E-FKH1 | Hikari | 82.516 | 1.498 |
| $BaF_2$ | Fluorite | 81.863 | |
| N-PK52 | Schott | 81.633 | 1.497 |
| E-FK01 | Hikari | 81.630 | 1.497 |
| FCD1 | Hoya | 81.608 | 1.497 |
| S-FPL51 | Ohara | 81.541 | 1.497 |
| K-PFK80 | Sumita | 81.363 | 1.497 |
| S-FPL51Y | Ohara | 81.138 | 1.497 |

In most embodiments, the indirect diagnostic ophthalmic lens systems (or devices or assemblies) of the presently described embodiments will have a single lens element made from a homogenous transparent material having an Abbe Number, $V_d$ greater than 80. This improves on the existing state-of-the-art. The lens element according to the presently described embodiments may be formed using any suitable technique.

Figure 4:
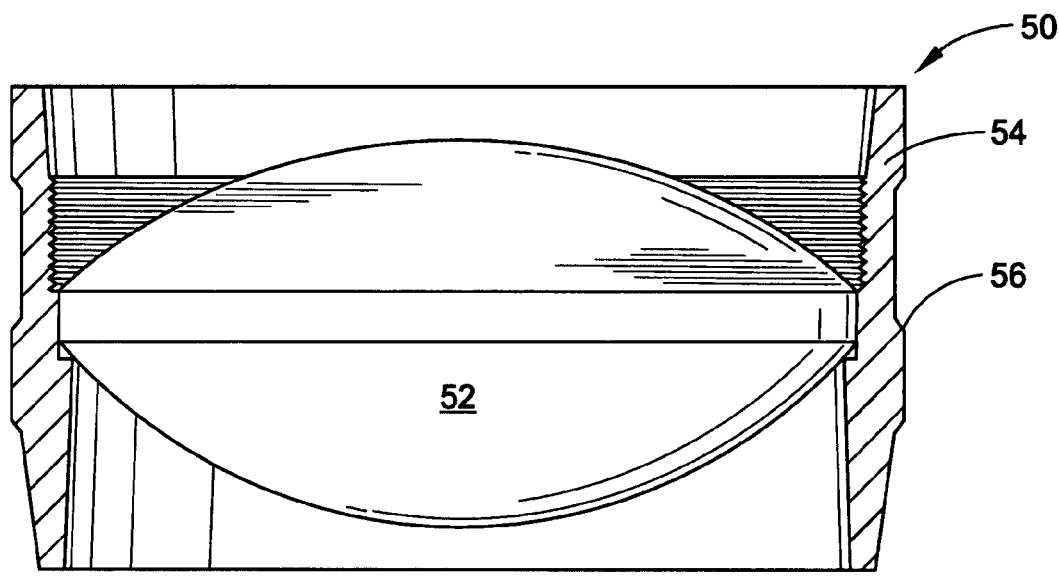
FIG. 4 shows a cross-sectional view of an exemplary lens mounted in a housing as one example of an embodiment of those presently described.

As should be apparent from FIGS. 1, 2 and 4, the front and rear surfaces of the lens element may each be aspheric or spherical. In other words, both surfaces may be aspheric, both may be spherical, or one may be aspheric and the other spherical. (As used herein, the "rear surface" of the lens element refers to the surface, which is positioned closest to the patient's eye during normal use).

Diagnostic ophthalmic lenses of the presently described embodiments may be configured to have a variety of optical properties. For example, for use in conjunction with an Indirect Ophthalmoscope, a diagnostic ophthalmic lens of the presently described embodiments, in one form, may have an optical power of between about 10 and about 55 diopters. Further, for use in conjunction with a Slit Lamp Biomicroscope, a diagnostic ophthalmic lens of the presently described embodiments, in one form, may have an optical power of between about 60 and about 130 diopters.

FIG. 4 shows a cross-section of a single element diagnostic ophthalmic lens assembly or device 50 according to an embodiment of the presently described embodiments. To form the assembly, the lens element is formed of suitable material (e.g. extra-low dispersion material or material having an Abbe number greater than 80). Then, the lens element, such as a lens or lens element 52, is mounted or positioned in a housing 54, which holds the lens element around its periphery. The housing 54 may take a variety of suitable forms and serves to protect the lens element 52 while also allowing an unobstructed optical pathway through its central aperture. In one form, the housing 54 may also have a tactile surface (e.g., a knurled or scalloped surface) machined or otherwise provided on its external surface 56. During normal hand-held usage, a doctor may adjust the position and orientation of the diagnostic ophthalmic lens 50 by manually grasping the housing 54 and then orienting it into proper relationship with respect to a patient's eye so that a viewing of, for example, the retinal surface can be had through use of, for example, the noted Indirect Opthalmoscope or Slit Lamp Biomicroscope. The tactile surface 56 facilitates that the prospect of the doctor obtaining a firm grip on the housing during the diagnostic application of the lens.

Figure 5:
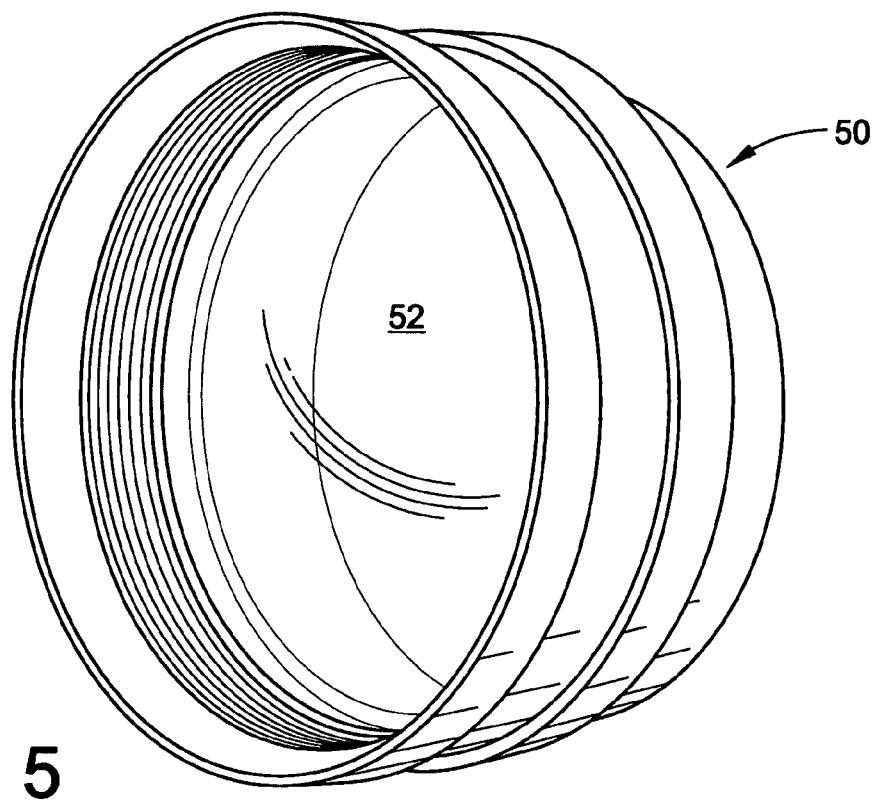
FIG. 5 is a perspective view of the lens of FIG. 4.

FIG. 5 shows a perspective view of the lens 50 of FIG. 4. As alluded to above, the housing 54 and lens element 52 may also be placed in a mounting structure for use with the noted optical devices. In either case, however, in one form, the lens element 52 is positioned within the housing 54 in any of a variety of manners. For example, threads (as shown in FIG. 4, for example) may be provided, for example, for a retaining ring within the housing to allow for suitable positioning of the lens element. A snap or friction fit may also be used. In addition, adhesives may be used as an alternative to or in combination with the threading or friction/snap fitting.

The specific illustrations and embodiments described herein are exemplary only in nature and are not intended to be limiting of that defined by the claims. Further embodiments and examples will be apparent to one of ordinary skill in the art in view of this specification and are within the scope of the claims.

What is claimed is:

1. A diagnostic ophthalmic lens assembly comprising:
   a single lens element formed from a homogenous material having an Abbe Number greater than 96 ($V_d > 96$); and,
   a housing in which said lens element is positioned.

2. The diagnostic ophthalmic lens assembly of claim 1, wherein surfaces of the lens element are aspheric.

3. The diagnostic ophthalmic lens assembly of claim 1, wherein surfaces of the lens element are spherical.

4. The diagnostic ophthalmic lens assembly of claim 1, wherein one surface of the lens element is aspheric and another surface of the lens element is spherical.

5. The diagnostic ophthalmic lens assembly of claim 1, wherein said lens assembly is used in conjunction with an Indirect Opthalmoscope.

6. The diagnostic ophthalmic lens assembly of claim 1, wherein the optical power of said lens element is about 10 to about 55 diopters.

7. The diagnostic ophthalmic lens assembly of claim 1, wherein said lens assembly is used in conjunction with a Slit Lamp Biomicroscope.

8. The diagnostic ophthalmic lens assembly of claim 1, wherein the optical power of said lens element is about 60 to about 130 diopters.

9. The diagnostic ophthalmic lens assembly of claim 1 wherein the material is a fluor-crown glass.

10. The diagnostic ophthalmic lens assembly of claim 1 wherein the material is extra-low dispersion glass.

11. The diagnostic ophthalmic lens assembly of claim 1 wherein the material is a fluorite.

12. The diagnostic ophthalmic lens assembly of claim 1 wherein the material is a polymer.

13. A method for forming a diagnostic ophthalmic lens assembly comprising:
    forming a single lens element for diagnostic ophthalmic use from an extra-low dispersion, homogenous material having an Abbe Number greater than 96; and,
    positioning the lens element within a housing.

14. The method of claim 13 further comprising using the lens assembly in conjunction with an Indirect Opthalmoscope.

15. The method of claim 13 further comprising using the lens assembly in conjunction with a Slit Lamp Biomicroscope.

16. A diagnostic ophthalmic lens system comprising:
    a single lens element formed from an Extra-low dispersion, homogenous material having an Abbe Number greater than 96; and,
    a housing in which the lens element is positioned.

17. The system of claim 16 further comprising an Indirect Opthalmoscope.

18. The system of claim 16 further comprising a Slit Lamp Biomicroscope.

* * * * *